US011801079B2

(12) United States Patent
Evans et al.

(10) Patent No.: US 11,801,079 B2
(45) Date of Patent: Oct. 31, 2023

(54) ROTATIONAL GUIDED GROWTH DEVICES, SYSTEMS, AND METHODS

(71) Applicant: University of Utah Research Foundation, Salt Lake City, UT (US)

(72) Inventors: Zackery Evans, Woods Cross, UT (US); T. Wade Fallin, Hyde Park, UT (US); Peter M. Stevens, Salt Lake City, UT (US)

(73) Assignee: UNIVERSITY OF UTAH RESEARCH FOUNDATION, Salt Lake City, UT (US)

( * ) Notice: Subject to any disclaimer, the term of this patent is extended or adjusted under 35 U.S.C. 154(b) by 0 days.

(21) Appl. No.: 17/958,566

(22) Filed: Oct. 3, 2022

(65) Prior Publication Data
US 2023/0149061 A1    May 18, 2023

Related U.S. Application Data

(62) Division of application No. 17/525,847, filed on Nov. 12, 2021, now Pat. No. 11,457,965.

(51) Int. Cl.
| A61B 17/80 | (2006.01) |
| A61B 17/86 | (2006.01) |
| A61B 17/56 | (2006.01) |
| A61B 17/70 | (2006.01) |

(52) U.S. Cl.
CPC ........ A61B 17/808 (2013.01); A61B 17/8061 (2013.01); A61B 17/8625 (2013.01);
(Continued)

(58) Field of Classification Search
CPC .............. A61B 17/808; A61B 17/8061; A61B 17/8625; A61B 17/80; A61B 17/8085;
(Continued)

(56) References Cited

U.S. PATENT DOCUMENTS

| 5,951,557 A | * | 9/1999 | Luter ..................... A61B 17/80 606/71 |
| 2004/0111089 A1 | * | 6/2004 | Stevens .............. A61B 17/1764 606/907 |

(Continued)

FOREIGN PATENT DOCUMENTS

CN        107684455 A      2/2018

OTHER PUBLICATIONS

International Search Report dated Mar. 23, 2023 for corresponding PCT Application No. PCT/US2022/045514.

*Primary Examiner* — Marcela I. Shirsat
(74) *Attorney, Agent, or Firm* — David Meibos; Maywood IP Law (57) ABSTRACT

A tether assembly may be attached to a bone to correct a rotational deformity. The bone may have a growth plate that separates a first section of the bone from a second section of the bone. The tether assembly may have a tether member with a first end, a second end, and a central portion extending between the first end and the second end. The first end may have a closed outer wall that defines and fully bounds a first aperture. The second end may have an open outer wall that defines and partially bounds a second aperture. The open outer wall may define a slot in communication with the second aperture. The first and second ends may be securable to the first and second sections of the bone via coupling members inserted through the first and second apertures and anchored in the first and second sections, respectively.

24 Claims, 7 Drawing Sheets

(52) U.S. Cl.
CPC ....... *A61B 17/7059* (2013.01); *A61B 17/8014* (2013.01); *A61B 17/8023* (2013.01); *A61B 2017/564* (2013.01)

(58) Field of Classification Search
CPC ..... A61B 17/82; A61B 17/88; A61B 17/7059; A61B 17/8014; A61B 17/1739; A61B 17/1764; A61B 17/155; A61B 17/0642; A61B 2017/564
USPC ........ 606/280, 281, 283–287, 293, 298–299, 606/86 R, 86 B
See application file for complete search history.

(56) References Cited

U.S. PATENT DOCUMENTS

| | | | |
|---|---|---|---|
| 2006/0142767 A1* | 6/2006 | Green | A61B 17/8061 606/281 |
| 2008/0306550 A1 | 12/2008 | Matityahu | |
| 2011/0106169 A1* | 5/2011 | Zalenski | A61B 17/808 606/279 |
| 2012/0016427 A1 | 1/2012 | Stindel et al. | |
| 2012/0209338 A1* | 8/2012 | Groiso | A61B 17/0642 140/71 R |
| 2015/0257803 A1* | 9/2015 | Sampath | A61B 17/809 606/281 |
| 2018/0021050 A1* | 1/2018 | Little | A61B 17/8057 606/280 |
| 2020/0038079 A1* | 2/2020 | Windolf | A61B 17/842 |
| 2020/0323569 A1* | 10/2020 | Venturini | A61B 17/80 |

* cited by examiner

Start Angle (degrees) / Treatment Time (months)

| Plate Length | 20 mm | | 26 mm | | 32 mm | |
|---|---|---|---|---|---|---|
| Femur Width / Correction | 54 mm | 59 mm | 60 mm | 66 mm | 67 mm | 72 mm |
| 10 degrees | 60 / 3 | 59 / 3 | 63 / 3 | 61 / 3 | 64 / 3 | 63 / 3 |
| 15 degrees | 52 / 5 | 50 / 5 | 56 / 5 | 54 / 5 | 58 / 5 | 56 / 6 |
| 20 degrees | 43 / 7 | 40 / 9 | 49 / 7 | 46 / 9 | 52 / 8 | 49 / 9 |
| 25 degrees | -- | -- | 41 / 11 | 36 / 13 | 45 / 11 | 42 / 13 |
| 30 degrees | -- | -- | -- | -- | 37 / 16 | 33 / 18 |

Fig. 9

ROTATIONAL GUIDED GROWTH DEVICES, SYSTEMS, AND METHODS

CROSS-REFERENCE TO RELATED APPLICATIONS

The present application is a divisional of U.S. patent application Ser. No. 17/525,847 filed on Nov. 12, 2021, entitled "Rotational Guided Growth Devices, Systems, and Methods, which is incorporated herein by reference in its entirety.

TECHNICAL FIELD

The present disclosure relates to bone fixation devices, systems, and methods. More specifically, the present disclosure relates to tether assemblies, systems, and methods for surgically changing the rotational alignment of intact bones.

BACKGROUND

In orthopedics, rotational deformities of the bones of the lower extremities can change the relative orientation between various anatomical features of the hip, knee, and ankle. For example, in the femur, angulation of the femoral neck in the upper femur with respect to the transcondylar axis of the lower femur is referred to as femoral anteversion. In normal human development, femoral anteversion is generally about 11°. FIG. 1B is a superior view of a femur over the bones of a foot, with normal anteversion, enabling proper gait with the foot facing forward.

Figure 2A:
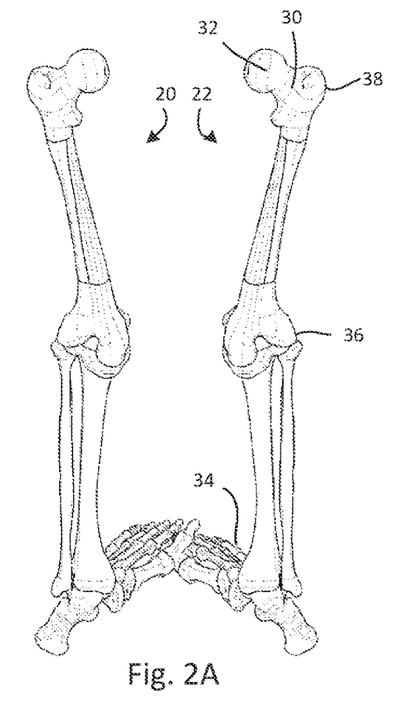
FIG. 2A is a posterior view of the lower skeletal extremities with abnormal anteversion.
Figure 2B:
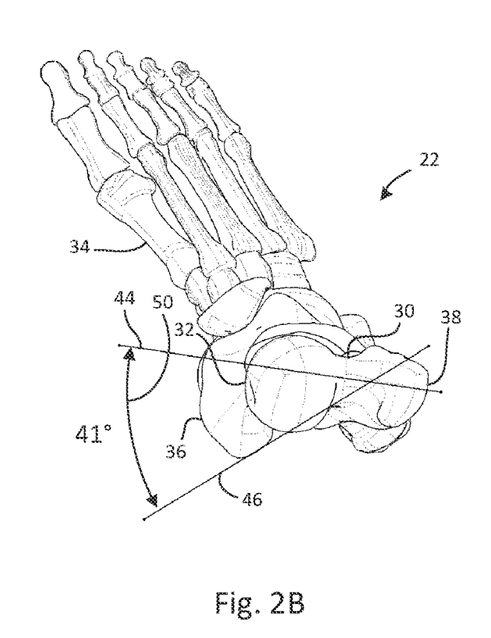
FIG. 2B is a superior view of the right lower extremity in FIG. 2A.

In contrast to normal human development, FIG. 2B illustrates an abnormal femoral anteversion angle of about 41°, or 30° of abnormal anteversion. This abnormal femoral anteversion results in a knee that twists inward relative to the hip, which results in "in-toeing" of the foot. This may predispose a patient to joint injuries at either end of the femur, such as ligament or labrum injuries in the hip joint and patella dislocations or ligament (e.g., anterior cruciate ligament) injuries in the knee joint. Persistent rotational deformity due to anteversion cannot be corrected with a brace or with physical therapy. Rotational deformities are also referred to as torsional deformities. In either case, these terms refer to the orientation of anatomic features relative to the long axis of the bone.

The current standard-of-care surgical remedy for anteversion is a rotational osteotomy of the femur. The femur is severed and the superior and inferior segments are re-attached to each other at a relative orientation that provides proper anteversion. This typically requires internal fixation with a large plate or intramedullary rod that is usually removed once the bone has healed after the procedure.

Specifically, during a traditional correction procedure for abnormal femoral anteversion, called a femoral de-rotation osteotomy, the surgeon cuts the femur perpendicular to the long axis of the bone, rotates the distal portion outward, typically about 20° to 30°, relative to the proximal end of the bone to achieve the correct rotational alignment, and then reattaches the transected bone portions together. A large bone plate or an intramedullary rod is then implanted to hold the transected bone portions in a corrected rotational alignment. However, this surgery is extremely invasive and associated with many negative side effects. Some of the negative side effects associated with this procedure include: (1) significant pain associated with bone cutting and healing; (2) relatively large incision and resulting large scar with increased risk of surgical site infection and wound complications, (3) delayed walking for weeks and sometimes months after the procedure to protect the bone while it heals; (4) risk of loss of bone fixation or implant failure and subsequent reoperation; (5) risk of delayed bone healing; (6) risk of non-union of the bone; (7) risk of neurovascular injury, etc. Accordingly, improved implant devices, systems, and methods that can alleviate some, or all, of these negative side effects would be desirable.

SUMMARY

The various implant devices, systems, and methods of the present disclosure have been developed in response to the present state of the art, and in response to the problems and needs in the art that have not yet been fully solved by currently available implant devices, systems, and methods. In some embodiments, the implant devices, systems, and methods of the present disclosure may provide improved rotational correction of the long bones of the lower extremities.

In some embodiments, a tether assembly may be attached to a bone to correct a rotational deformity in a bone, such as femoral anteversion. The bone may have a growth plate that separates a first section of the bone from a second section of the bone. The tether assembly may have a tether member with a first end, a second end, and a central portion extending between the first end and the second end. The first end may have a closed outer wall that defines and fully bounds a first aperture. The second end may have an open outer wall that defines and partially bounds a second aperture. The open outer wall may define a slot in communication with the second aperture. The first and second ends may be securable to the first and second sections of the bone via coupling members inserted through the first and second apertures and anchored in the first and second sections, respectively.

The tether assembly may further include the first coupling member, which may have a first head and a first shank with a first bone engagement feature configured to retain the first shank in the bone. The tether assembly may further include the second coupling member, which may have a second head and a second shank with a second bone engagement feature configured to retain the second shank in the bone.

The second shank may have a second shank width and the second head may have a second head width. The second shank width and/or the second head width may not be smaller than a corresponding portion of the slot through which it must pass in order to exit the second aperture through the slot, such that the second coupling member is movable through the slot only in response to exertion of a threshold level of tension between the second coupling member and the second end.

The corresponding portion of the slot may be configured to deform elastically to permit passage of the second shank therethrough in response to exertion of the threshold level of tension.

At least one of the first head and the second head may have a spherical surface. The corresponding one of the first aperture and the second aperture may have a complementary spherical surface sized to receive the spherical surface to provide adjustable positioning of the first head or the second head relative to the first aperture or the second aperture.

The central portion may have a contoured shape created by projecting an elongate area defined on a sagittal plane onto a medial epicondylar bone surface or a lateral epicondylar bone surface of a pediatric distal femur. The elongate area may have a long axis and a short axis orthogonal to the long axis.

The long axis as measured on the sagittal plane may be positioned at an angle relative to a transverse plane. The angle may be within the range of 30° to 60°.

The slot may be oriented nonperpendicular to a longitudinal length of the central portion.

The slot may be oriented at an angle relative to the longitudinal length. The angle may be within the range of 30° to 80°.

In some embodiments, a tether assembly may be attachable to a bone to correct a rotational deformity in a bone, such as femoral anteversion. The bone may have a growth plate that separates a first section of the bone from a second section of the bone. The tether assembly may have a first coupling member with a first head and a first shank with a first bone engagement feature configured to retain the first shank in the bone. The tether assembly may further have a second coupling member with a second head and a second shank with a second bone engagement feature configured to retain the second shank in the bone. The tether assembly may further have a tether member with a first end, a second end, and a central portion extending between the first end and the second end. The first end may be configured to engage the first head to nonreleasably secure the first end to the first section of the bone. The second end may be configured to engage the second head to releasably secure the second end to the second section of the bone such that, in response to exertion of a threshold level of tension between the second coupling member and the second end, the second end is released from the second section of the bone.

The first end may have a fully-bounded first aperture. The second end may have a partially-bounded second aperture that is accessible via a slot.

The second shank may have a second shank width that is not smaller than a slot width of the slot and is movable through the slot in response to exertion of the threshold level of tension.

The slot may be configured to deform elastically to permit passage of the second shank therethrough in response to exertion of the threshold level of tension.

The slot may be oriented nonperpendicular to a longitudinal length of the central portion.

At least one of the first head and the second head may have a spherical surface. The corresponding one of the first end and the second end may have a complementary spherical surface sized to receive the spherical surface to provide adjustable positioning of the first head or the second head relative to the first end or the second end.

The central portion may have a contoured shape created by projecting an elongate area defined on a sagittal plane onto a medial epicondylar bone surface or a lateral epicondylar bone surface of a pediatric distal femur. The elongate area may have a long axis and a short axis orthogonal to the long axis.

In some embodiments, a method may be used to perform rotational deformity correction on a bone with a growth plate that separates a first section of the bone from a second section of the bone. The method may include positioning a tether member of a tether assembly on the bone. The tether assembly may include a first coupling member with a first head and a first shank with a first bone engagement feature configured to retain the first shank in the bone, a second coupling member with a second head and a second shank with a second bone engagement feature configured to retain the second shank in the bone, and the tether member. The tether member may have a first end, a second end, and a central portion extending between the first end and the second end. The method may further include, with the first coupling member, securing the first end of the tether member to the first section of the bone, and, with the second coupling member, releasably securing the second end of the tether member to the second section of the bone such that, in response to exertion of a threshold level of tension between the second coupling member and the second end, the second end is released from the second section of the bone.

The first end may have a fully-bounded first aperture. The second end may have a partially-bounded second aperture that is accessible via a slot. Securing the first end to the first section may include inserting the first shank through the first aperture and anchoring the first shank to the first section. Releasably securing the second end to the second section may include inserting the second shank through the second aperture and anchoring the second shank to the second section.

The slot may be oriented nonperpendicular to a longitudinal length of the central portion.

Each of the first head and the second head may have a spherical surface. Each of the first end and the second end may have a complementary spherical surface. Securing the first end to the first section may include receiving the spherical surface of the first head in the complementary spherical surface of the first end to provide adjustable positioning of the first head relative to the first end. Securing the second end to the second section may include receiving the spherical surface of the second head in the complementary spherical surface of the second end to provide adjustable positioning of the second head relative to the second end.

These and other features and advantages of the present disclosure will become more fully apparent from the following description and appended claims or may be learned by the practice of the devices, systems, and methods set forth hereinafter.

BRIEF DESCRIPTION OF THE DRAWINGS

Exemplary embodiments of the present disclosure will become more fully apparent from the following description taken in conjunction with the accompanying drawings. Understanding that these drawings depict only exemplary embodiments and are, therefore, not to be considered limiting of the scope of the present disclosure, the exemplary embodiments of the present disclosure will be described with additional specificity and detail through use of the accompanying drawings in which.

It is to be understood that the drawings are for purposes of illustrating the concepts of the present disclosure and may be drawn to scale, or may include variations from scale drawings. Furthermore, the drawings illustrate exemplary embodiments and do not represent limitations to the scope of the present disclosure.

DETAILED DESCRIPTION

Exemplary embodiments of the present disclosure will be best understood by reference to the drawings, wherein like parts are designated by like numerals throughout. It will be readily understood that the components of the present disclosure, as generally described and illustrated in the drawings, could be arranged, and designed in a wide variety of different configurations. Thus, the following more detailed description of the embodiments of the implants, systems, and methods, as represented in the drawings, is not intended to limit the scope of the present disclosure, but is merely representative of exemplary embodiments of the present disclosure.

The word "exemplary" is used herein to mean "serving as an example, instance, or illustration." Any embodiment described herein as "exemplary" is not necessarily to be construed as preferred or advantageous over other embodiments. While the various aspects of the embodiments are presented in the drawings, the drawings are not necessarily drawn to scale unless specifically indicated.

The following examples have been included to provide guidance to one of ordinary skill in the art for practicing representative embodiments of the presently disclosed subject matter. In light of the present disclosure and the general level of skill in the art, those of skill in the art can appreciate that the following examples are intended to be exemplary only and that numerous changes, modifications, and alterations can be employed without departing from the scope of the presently disclosed subject matter.

It will be understood that any feature of any embodiment described or contemplated herein may be combined with any other embodiment that is described or contemplated herein without departing from the spirit or scope of the present disclosure.

Figure 1A:
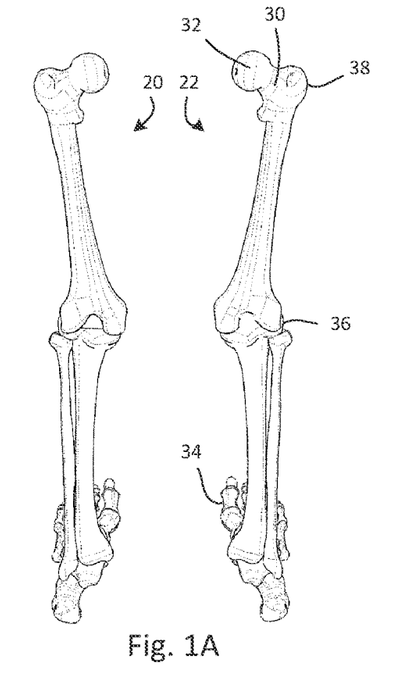
FIG. 1A is a posterior view of lower skeletal extremities with normal anteversion.
Figure 1B:
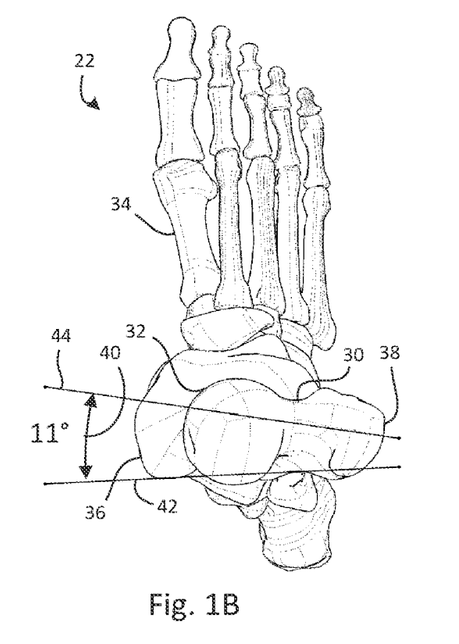
FIG. 1B is a superior view of the right lower extremity in FIG. 1A.

FIG. 1A is a posterior view (i.e. a view from a posterior viewpoint) of the lower skeletal extremities showing normal alignment of the left extremity 20 and the right extremity 22 in the pediatric population. FIG. 1B is a superior view of the right extremity 22, showing the anteversion of the femoral neck 30 and femoral head 32. It can be appreciated in FIG. 1B that the foot 34 is well aligned with the knee 36 and the hip 38. Anteversion is the angle, or anteversion angle 40, measured between a line 42 tangent to the posterior condyles of the distal femur, also referred to herein as the transcondylar axis, and a line 44 that bisects the femoral neck and head. In FIG. 1B, the anteversion angle 40 is 11°, which is considered to be within the normal range in the general pediatric population.

FIG. 2A is a posterior view of the left extremity 20 and the right extremity 22 showing an abnormal alignment of the left extremity 20 and the right extremity 22 in the pediatric population. FIG. 2B is a superior view of the right extremity 22, showing the anteversion of the femoral neck 30 and femoral head 32. It can be appreciated in FIG. 2B that the foot 34 and the knee 36 are turned inward relative to the hip 38. In FIG. 2B, the anteversion angle 50 is 41° (measured between the line 44 that bisects the femoral neck and head and a line 46 tangent to the posterior condyles of the distal femur), which is outside the normal range in the general pediatric population. This abnormal anteversion is observed as "in-toeing" of the feet, causing the left foot to be over rotated in the clockwise direction and the foot 34 to be over rotated in the counterclockwise direction, as viewed when looking down at the feet from a standing position. Abnormal anteversion is also referred to as a rotational or torsional deformity, as it represents an angular abnormality as viewed along the long axis of the bone. It can cause "in-toeing" as mentioned above, or splay the foot outward. Either can beneficially be corrected via the present disclosure. Although anteversion is used as a specific example, those of skill in the art will recognize that the techniques, implants, and principles taught by this disclose may be applied to other rotational deformities in femurs and/or other bones.

FIG. 2A provides an example of a bilateral femoral rotational deformity, which is common when femoral rotational deformity is present; however, unilateral femoral rotational deformities are also occasionally present in the pediatric population. Although the preceding discussion is limited to the femur, it is understood that rotational defects can exist in other bones of the extremities, such as the tibia, and that the devices, systems and methods presented herein are equally applicable to other extremity bones, including but not limited to any other bones of the legs, feet, arms or hands.

Figure 3A:
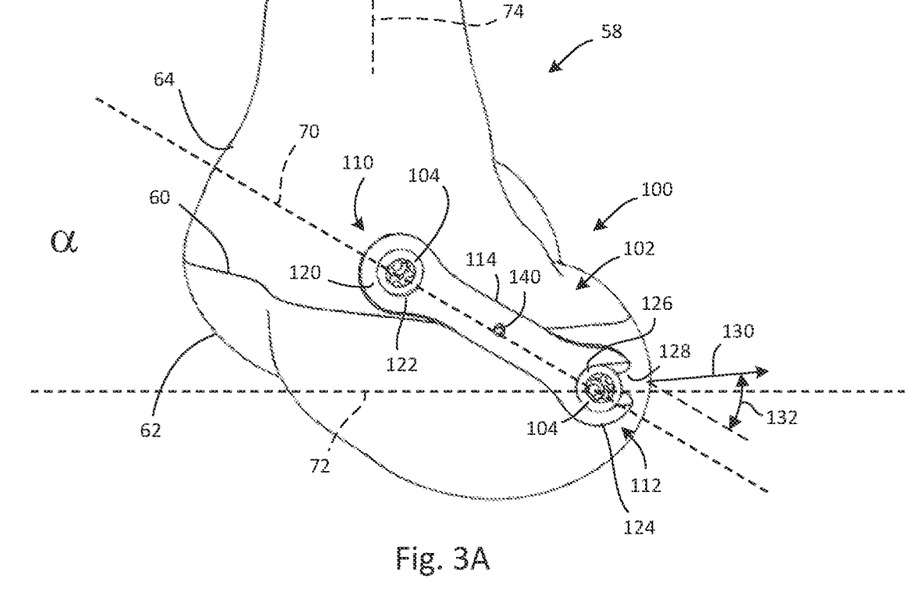
FIG. 3A is a medial view of a right pediatric knee with a tether assembly according to one embodiment attached to the femur, at the time of surgery.

FIG. 3A is a medial view of the distal portion of a femur 58 showing a physis 60, also referred to as a growth plate, and showing an embodiment of the present invention. The femur 58 may have an epiphyseal section 62 distal to the physis 60, and a metaphyseal section 64 proximal to the physis 60. The physis 60 may separate the epiphyseal section 62 from the metaphyseal section 64. The femur 58 may be a pediatric femur, which may continue to grow longitudinally from the physis 60.

Coupled to the distal portion of the femur 58 is a tether assembly 100, which may include a tether member 102, also referred to herein as a "bone plate," and two coupling members 104, which are also referred to herein as "bone screws." The tether member 102 may have a first end 110, a second end 112, and a central portion 114 extending between the first end 110 and the second end 112.

The tether member 102 may be fabricated from any of a variety of rigid biocompatible materials, such as but not limited to: stainless steel, titanium and its alloys, nickel titanium alloy, polyetheretherketone (PEEK), carbon fiber reinforced PEEK, biodegradable polymers such as poly-L-lactic acid (PLLA), and combinations of the foregoing. Alternatively, the tether member 102 may be formed of flexible biocompatible textiles, such as those used for sutures or surgical meshes. Alternatively, the tether member 102 may be a hybrid construct in which the central portion 114 is comprised of a flexible textile material and the first end 110 and the second end 112 are comprised of a rigid material. Alternatively, the tether member 102 may be formed of a composite material using any of the aforementioned polymers as a matrix and any of the aforementioned textiles as fiber reinforcement of the matrix. Composite material may be customized to provide high stiffness and strength in the direction of highest tensile stresses, such as along a longitudinal axis of the tether member 102, but provide more flexibility and compliance in other directions, to allow the tether member 102 to better conform to the contours of the bone surface of the distal portion of the femur 58. In some embodiments, the tether member 102 may be resorbable.

The coupling members 104 may be fabricated from any of the rigid biocompatible materials listed above for the tether member 102, so long as the material used for the coupling members 104 is electrochemically and mechanically compatible with the material used for the tether member 102. The coupling members 104 may be type of bone screws known in the orthopedic arts. In alternative embodiments (not shown), coupling members may include staples, suture anchors, pins, tacks and/or other bone fastening devices known to those skilled in the art. Coupling members may also be made resorbable if desired.

The tether member 102 shown in FIG. 3A may be coupled to the medial side of the distal portion of the femur 58, which may be a right femur. The first end 110 and the second end 112 of the tether member 102 may each be secured to the femur 58 by one of the coupling members 104.

The central portion 114 of the tether member 102 may be elongated in shape, with a length, extending along a longitudinal axis 70 passing through the first end 110 and the second end 112, that is greater than its width transverse to the longitudinal axis. The first end 110 may have a closed outer wall 120 and a first aperture 122 fully bounded by the closed outer wall 120. The second end 112 may have an open outer wall 124 and a second aperture 126 bounded by the open outer wall 124. The open outer wall 124 may define an opening, or slot 128, through which the associated one of the coupling members 104 may be removed from the second aperture 126 along a direction 130 that is generally in-plane with, and nonperpendicular to, the tether member 102. By contrast, the associated one of the coupling members 104 retained within the first aperture 122 may only be withdrawable from the first aperture 122 along a direction generally perpendicular to the tether member 102 (i.e., out of the page, in the view of FIG. 3A).

As shown, the slot 128 may oriented nonparallel and/or nonperpendicular to the length of the central portion 114 of the tether member 102. Thus, an angle 132 may exist between the direction 130 and the longitudinal axis 70 of the tether member 102. The angle 132 may be a constant for all patients, or may be selected on a patient-specific basis to control the desired amount of anteversion correction. The angle 132 may be greater than 0° and less than 90°. Further, the angle 132 may be greater than 20° and less than 70°. Yet further, the angle 132 may be greater than 30° and less than 50°. Still further, the angle 132 may be greater than 35° and less than 45°. In some embodiments, the angle 132 may be about 40°.

As will be described in greater detail below, the slot 128 may enable the second end 112 to be releasably secured to the epiphyseal section 62. "Releasable" securement means the securement of two items together in a surgical setting such that they can be detached from each other by time or by the body after the surgery is complete, rather than requiring another surgical intervention to effect release. By contrast, "nonreleasable" securement means the securement of two items together in a surgical setting such that they cannot generally be detached from each other without another surgical intervention. The first end 110 may be nonreleasably secured to the metaphyseal section 64.

Use of a slotted aperture is only one mechanism capable of providing releasable securement. In alternative embodiments, releasable securement may be provided by making a tether member or coupling member weak enough to break under the desired conditions. For example, the tether member 102 could be modified to make the central portion 114 much thinner, and thus breakable under tension. Alternatively, one of the coupling members 104 could be modified to have a breakaway head or the like.

Returning to FIG. 3A, the longitudinal axis 70 may bisect the central portion 114 of the tether member 102. The tether member 102 may further have a third aperture 140 positioned approximately at the mid-point of the longitudinal axis 70. The third aperture 140 may be used to position the tether member 102 centrally over the physis 60 by aligning the third aperture 140 with the physis 60. This may be done visually by a surgeon installing the tether member 102, for example, by ensuring that the physis 60 is visible through the third aperture 140 when the tether member 102 is seated on the distal end of the femur 58. Additionally or alternatively, a guidewire or other instrument may be registered on or near the physis 60 and inserted through the third aperture 140 and into contact with the physis 60 to guide placement of the tether member 102 such that the third aperture 140 is placed on or near the physis 60.

The longitudinal axis 70 may be at an alignment angle α to a transverse axis 72 that is aligned with an anatomic transverse plane that is perpendicular to the longitudinal axis 74 of the femur 58. Angle α is referred herein as the "initial alignment angle."

Once the tether member 102 has been properly positioned on the femur 58, one of the coupling members 104 may be placed through the first aperture 122 to couple the tether member 102 to the anterior portion of the metaphyseal section 64 of the femur 58, proximal to the physis 60. Another of the coupling members 104 may be placed through the second aperture 126 to couple the tether member 102 to the posterior portion of the epiphyseal section 62, distal to the physis 60 and posterior to the first end 110. The coupling members 104 may advantageously be placed a minimum distance of 6 mm to 8 mm away from the central portion of the physis 60 to ensure that the coupling members 104 do not impede or interfere with the natural growth emanating from the physis 60. In alternative embodiments, the tether member 102 may be reversed, such that the first end 110 is secured to the metaphyseal section 64 and the second end 112 is secured to the epiphyseal section 62.

Figure 3B:
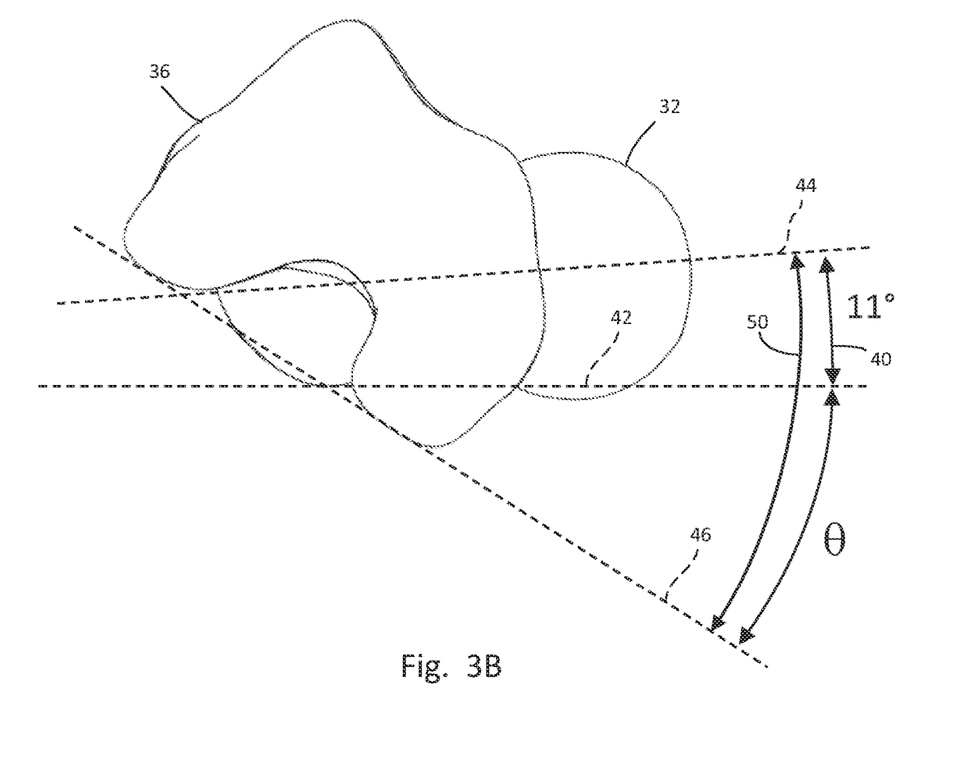
FIG. 3B is an inferior view of the femur of FIG. 3A.
Figure 4A:
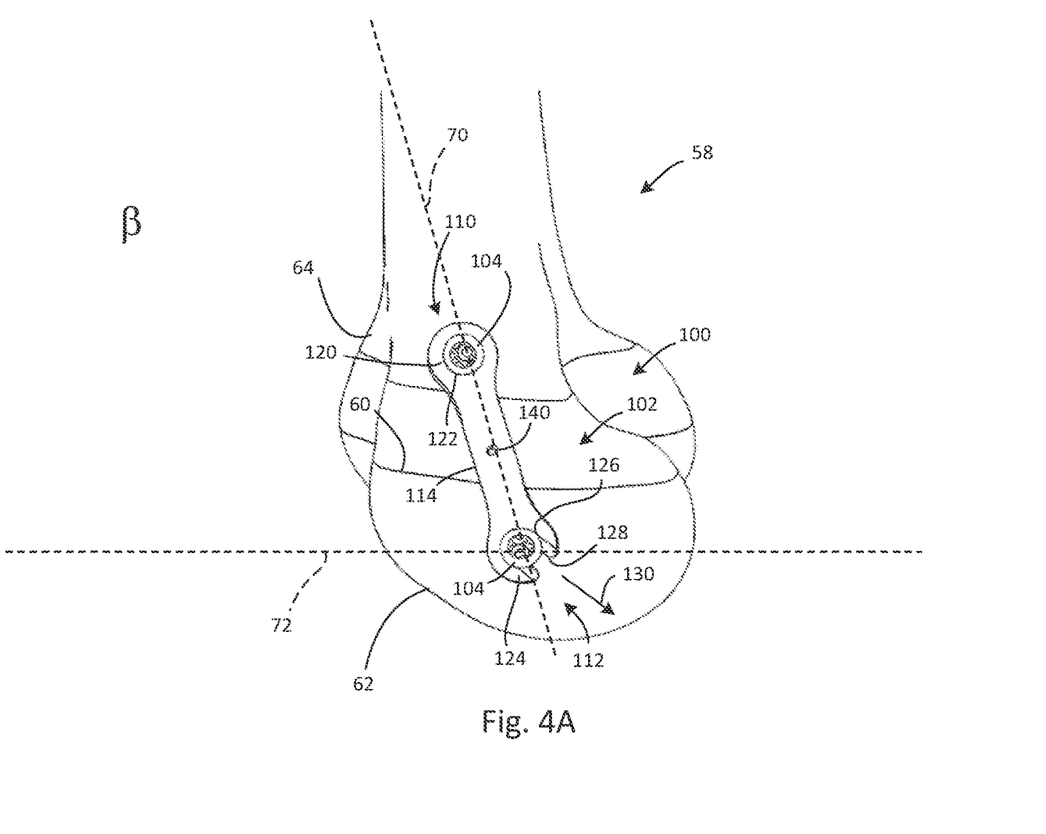
FIG. 4A is a medial view of a right pediatric knee with the tether assembly of FIG. 3A, at a first period after the surgery.
Figure 5A:
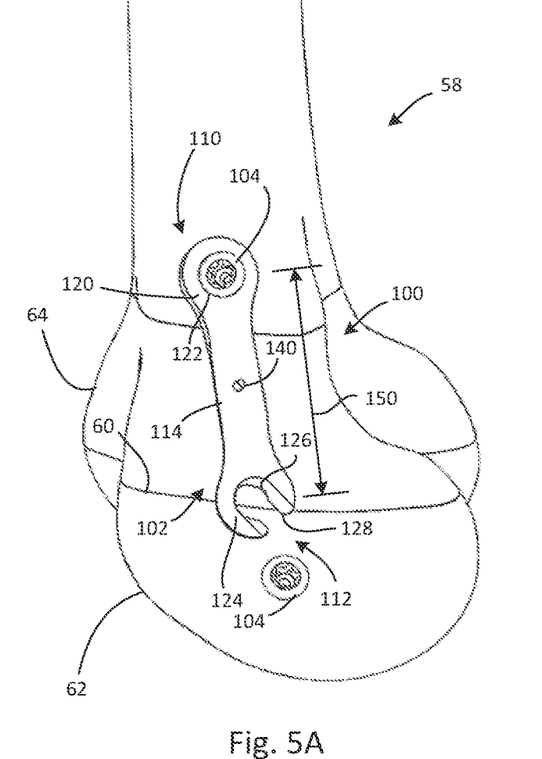
FIG. 5A is a medial view of a right pediatric knee with the tether assembly of FIG. 3A, at a second period after the surgery.

FIG. 3B shows the femur 58 of FIG. 3A without the tether assembly 100. It can be appreciated in FIG. 3A that the femur 58 has abnormal anteversion; the degree of abnormality is shown as the angle θ in FIG. 3B. This angle θ is the amount of anteversion in excess of the normal anteversion angle of 11°. The angle θ may be the anteversion angle 50 of FIG. 2B minus the anteversion angle 40 (11°) of FIG. 1B. It is desirable to correct the rotational deformity by rotating the distal end of the femur 58 by 8° relative to the proximal end of the femur 58, so that the posterior condyles of the femur 58 are restored to a normal alignment with the femoral neck and head of the femur 58. To ensure that the induced rotational change in the femur 58 is radially symmetric, a second tether assembly (not shown) may advantageously be placed on a second side of the femur 58. In the case of the distal end of the femur 58, the second tether assembly may be placed on the lateral side of the femur 58, opposite and radially symmetrical to the placement of the tether assembly 100 on the medial side as shown in FIGS. 3A, 4A and 5A.

Those of skill in the art will recognize that the use of two tether assemblies is optional. In some embodiments, only a single tether assembly may be used. A single tether assembly may be placed on the lateral, medial, anterior, or posterior sides of the femur 58, or even on the postero-lateral, antero-lateral, postero-medial, or antero-medial sides of the femur 58. In alternative embodiments, more than two tether assemblies may be used. In such cases, the tether assemblies may optionally be arranged and oriented in radially-symmetrical fashion about the distal end of the femur 58, and may be placed on any of the sides of the femur 58 set forth above. In further alternative embodiments, two tether assemblies may be used, and may be arranged differently than described above. For example, the tether assemblies need not necessarily be placed on the lateral and medial sides of the femur 58, but may be placed on any of the sides set forth above. Again, radial symmetry is optional.

Figure 4B:
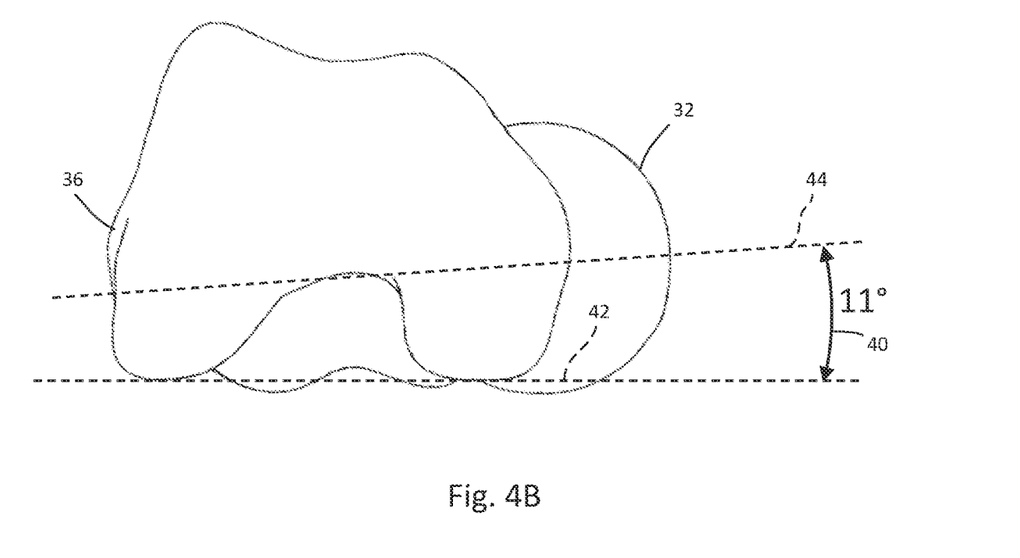
FIG. 4B is an inferior view of the femur of FIG. 4A.

FIGS. 3A and 3B illustrate the femur 58 and the tether assembly 100 at the time of a surgery in which the tether assembly 100 (and optionally one or more additional tether assemblies) are initially installed. FIGS. 4A and 4B Illustrate the femur 58 and tether assembly 100 shown in FIGS. 3A and 3B after a first period of time following the surgery. During the first period of time, natural growth of the femur 58 may occur, increasing the longitudinal spacing between the epiphyseal section 62 and the metaphyseal section 64. Due to the constraint of the tether assembly 100 (and optional one or more additional tether assemblies), some of the longitudinal growth of the femur 58 may be converted to a relative rotation, about the longitudinal axis 74, between the epiphyseal section 62 and the metaphyseal section 64, thereby reducing and eventually eliminating the abnormal anteversion of 8° that was initially present in the femur 58. The relative rotation between the epiphyseal section 62 and the metaphyseal section 64 may cause the tether member 102 to rotate from the initial alignment angle α (as shown in FIGS. 3A and 3B), relative to the transverse axis 72, to a terminal intermediate alignment angle β (as shown in FIGS. 4A and 4B).

Upon reaching the terminal alignment of @°, the changed alignment (relative to the transverse plane) of the slot in the tether member is such that the slot 128 of the second aperture 126 is oriented to permit withdrawal of the associated one of the coupling members 104 from the second aperture 126 in response to continued longitudinal growth of the femur 58. Thus, any further longitudinal growth of the femur 58 may cause the associated one of the coupling members 104 to move along the direction 130 to escape the second aperture 126. This may release the tether member 102 from attachment to the epiphyseal section 62, thereby permitting the femur 58 to elongate without further rotational adjustment.

Figure 5B:
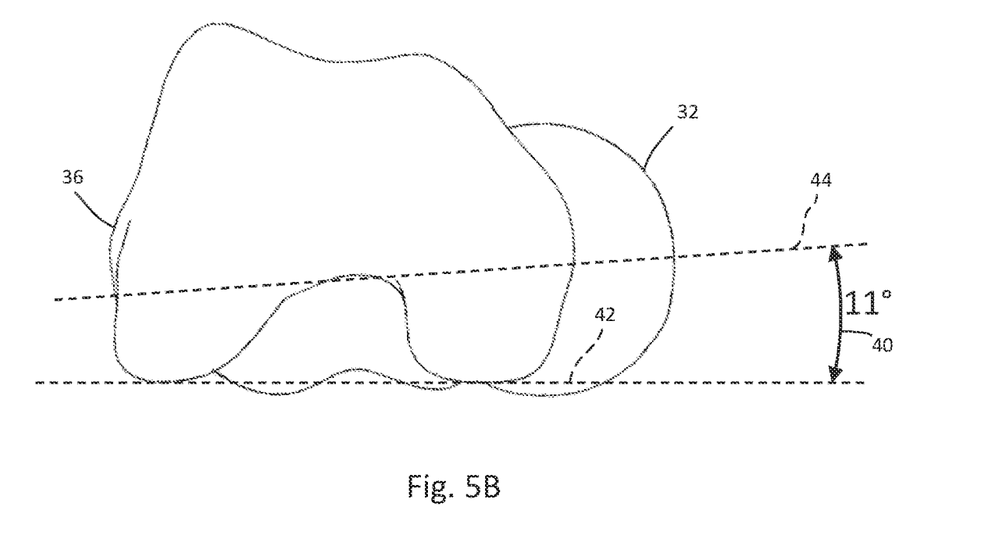
FIG. 5B is an inferior view of the femur of FIG. 5A.

The femur 58 shown in FIGS. 5A and 5B illustrates the femur 58 of FIGS. 3A, 3B, 4A and 4B after a second period following the surgery, where the second period is greater than the first period. During the interval of time after the first period until the end of the second period, additional longitudinal growth of the femur 58 has occurred, causing the one of the coupling members 104 previously captured in the second aperture 126 to traverse the length of the slot 128 of the second aperture 126 and to translate outside the outer perimeter of the second end 112 of the tether member 102. Thus, the amount of rotational correction as measured by the angle θ can be "programmed" into the surgical technique by selecting the right combination of α, β, and the distance 150 between the first aperture 122 and the second aperture 126 of the tether member 102 (referred to herein as "plate length") for a given diametrical width of a distal femur. The foregoing list of dimensional parameters have analytical geometry relationships that can be expressed in equation form to determine the right parameter values to achieve a target rotational correction angle θ.

It can be appreciated that the femur in FIG. 5B has an unchanged rotational alignment when compared to the femur in FIG. 4B, as the one of the coupling members 104 formerly captured in the second aperture 126 has escaped the tether member 102, and thus the constraint that forced the prior rotational change is no longer in effect. Furthermore, it may be advantageous to provide an "automated" removal of the constraint imposed by the tether member 102 once the rotational deformity in the femur 58 is corrected and before the tether member 102 migrates to a more vertical alignment with respect to the transverse plane. If the tether member 102 were to continue to constrain the distance between the coupling members 104 as it achieved vertical alignment, the tether member 102 would arrest further longitudinal growth of the femur 58. Indeed, such a constraint is known in the clinical literature as "shutting down the growth plate," a condition that permanently disables the ability of the growth plate, or physis 60, to generate new bone to continue the natural growth of the bone. Such a clinical condition can be very deleterious to the child, as it could lead to leg length discrepancies or failure to achieve normal height in adulthood.

Figure 6A:
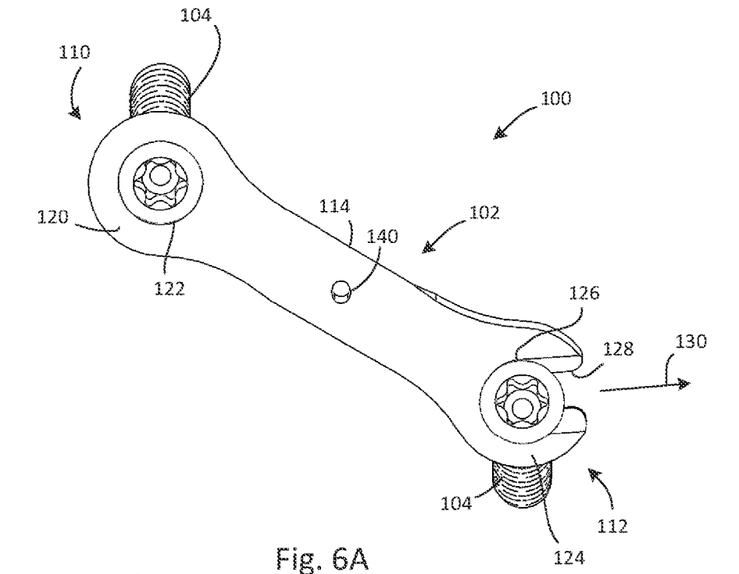
FIG. 6A is a top view of the tether assembly of FIG. 3A.
Figures 6B, 6C:
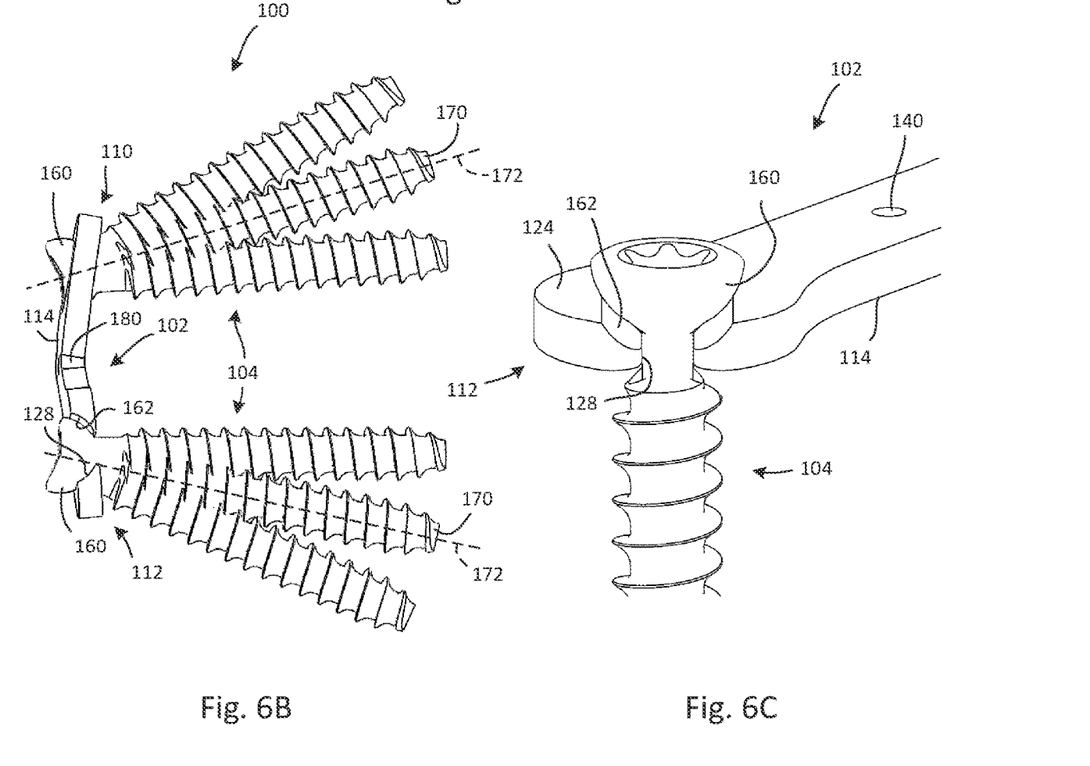
FIG. 6B is a side view of the tether assembly of FIG. 3A, showing the tether member with multiple potential orientations of each of the coupling members.
FIG. 6C is a close-up perspective view of the tether member and one coupling member of the tether assembly of FIG. 3A.

FIG. 6A is a top view of the tether assembly 100 of FIG. 3A, in isolation. The coupling members 104 are positioned in the first aperture 122 and the second aperture 126. FIG. 6B is a side view of the tether assembly 100 of FIG. 3A, illustrating how the coupling members 104 can articulate with the first aperture 122 and the second aperture 126 to allow a multitude of relative orientations between the tether member 102 and the coupling members 104. The aforementioned articulation may be achieved by having spherical surfaces 160 on the coupling members 104 and complementary spherical surfaces 162 on the first aperture 122 and the second aperture 126. The phrase "spherical surface" will be understood to require not an entire sphere, but any three-dimensional portion of a concave or convex spherical shape.

Each of the complementary spherical surfaces 162 may be a concave spherical segment defined between two spaced-apart parallel planes. One of these planes may be defined by the top surface of the first end 110 or the second end 112, as applicable, and the other may pass through the space between this top surface and the associated bottom surface. The second aperture 126 may further be bounded by a plane positioned at an angle to the two parallel planes to create the slot 128. A close-up view of the slot 128 is provided in FIG. 6C.

It is noted that the relative alignment of the mid-range articulation position 170 of each of the coupling members 104 relative to the tether member 102 is at a divergent angle. This is to help ensure that the coupling members 104 are directed away from the physis 60 when the tether member 102 is attached to the femur 58, as placement of the coupling members 104 into the physis 60 could inhibit the bone growth from the physis 60. While FIG. 6B shows the vertical range for orienting the coupling members 104 relative to the tether member 102, due to the spherical articulation described above, a similar range of motion may be present in all planes containing the axis 172 of each of the coupling members 104 located at its mid-range articulation position 170.

It can be further appreciated in FIGS. 6A and 6B that the tether member 102 has a three-dimensional contour. This contour may be selected to match that of the medial or lateral epicondylar bone surface, on which the tether member 102 is to be attached. Since the tether member 102 is to rotate on the associated bone surface in the course of correcting the anteversion of the bone, the tether member 102 may be contoured to match a portion of the bone that is angled between the initial and final alignment angles (for example, angled between α as shown in FIG. 3A and β as shown in FIG. 4A). The contour that is to be matched may thus be the portion of bone that will be overlaid by the tether member 102 partway through the anteversion correction process.

The central portion 114 of the tether member 102 may have a central bend 180 that exists as part of this contouring. The third aperture 140 may pass through the central bend 180. Further, the central portion 114 may have a central twist such that the first end 110 and the second end 112 are not in the same plane. As a result, the second aperture 126 may have an axis 176 that is not parallel to the axis 174 of the first aperture 122 (as shown in FIG. 7B).

In some embodiments, this contour may be created by projecting an elongate area defined on a sagittal plane onto one of the medial and lateral epicondylar bone surfaces of a representative pediatric distal femur, such as the femur 58. The elongate area may have a long axis and a short axis orthogonal to the long axis. The long axis, measured on the sagittal plane, may be positioned at an angle relative to a transverse plane, wherein the angle is less than 70°. The long axis is generally between 20° and 70°, preferably between 30° and 60°, and more preferably between 40° and 50°. The long axis may be at about 45°.

Figure 7A:
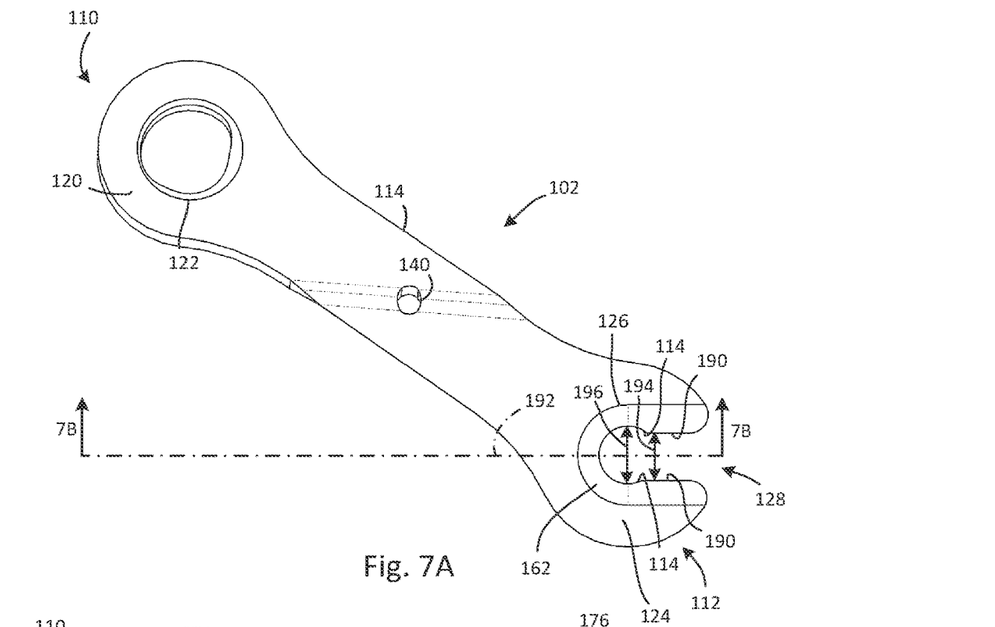
FIG. 7A is a top view of the tether member of the tether assembly of FIG. 3A.
Figure 7B:
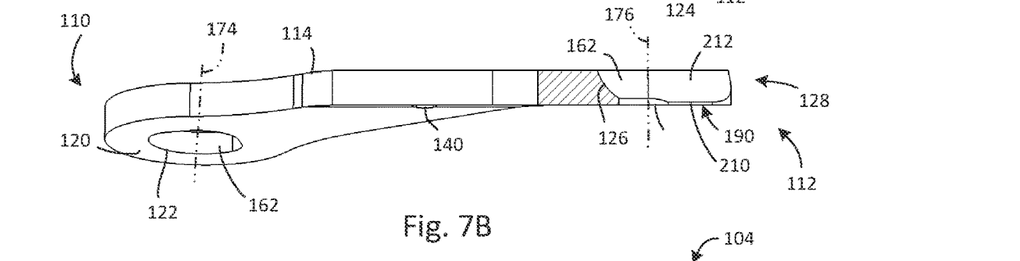
FIG. 7B is a side elevation, partial section view of the tether member of FIG. 3A.

FIG. 7A shows another top view of an embodiment of the tether member 102 of the tether assembly 100 of FIG. 3A, and FIG. 7B is a side elevation, partial sectional view of the tether member 102. As shown, the slot 128 may have side walls 190 and a slot axis 192 that is located between the side walls 190 and bisects the side walls 190. The section view shows the portion of the complementary spherical surface 162 of the second aperture 126 and also shows the side wall 190 on one slide of the slot 128. A portion of the slot 128 has a slot width 194 that is smaller than the diameter 196 of the second aperture.

Figure 8A:
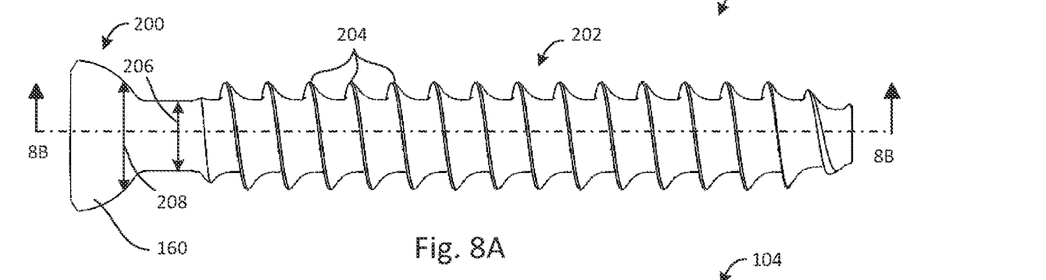
FIG. 8A is a side elevation view of a coupling member of the tether assembly of FIG. 3A.
Figure 8B:
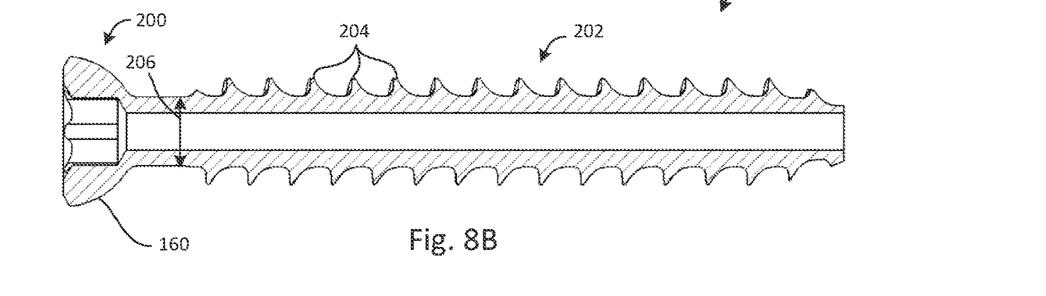
FIG. 8B is a side elevation, section view of the coupling member of FIG. 8A.

FIG. 8A is a side elevation view of one of the coupling members 104 of the tether assembly 100 of FIG. 3A. FIG. 8B is a side elevation, section view of one of the coupling members 104. Each of the coupling members 104 may be a bone screw or other bone fastening device of any type known in the orthopedic arts. As shown, each of the coupling members 104 may have a head 200 and a shank 202 extending from the head 200. The shank 202 may have a plurality of bone engagement features extending therefrom. As embodied in FIG. 8B, the bone engagement features may be screw threads 204.

The shank 202 may have a shank diameter 206 that is larger than the slot width 194 and smaller than the diameter 196 of the second aperture 126. The spherical surfaces 160 of the coupling members 104 may be on the head 200 of each of the coupling members 104. The spherical surfaces 160 may mate with the complementary spherical surface 162 of the first aperture 122 and the second aperture 126 to enable polyaxial articulation as set forth above. The relative sizing between the shank diameter 206 and the diameter 196 of the second aperture 126 may enable the spherical articulation between the second end 112 of the tether member 102 and the associated one of the coupling members 104 as demonstrated in FIG. 6B.

The shank 202 may be positioned in the second aperture 126 such that the shank diameter 206 is aligned with the slot 128 as shown in FIG. 6C. Thus, the shank 202 can pass through the slot 128, as described above. However, the relative sizing between the shank diameter 206 and the slot width 194 may be selected such that a threshold force must be applied between the tether member 102 and the shank 202 before the shank 202 passes through the slot 128. Specifically, the relatively smaller size of the slot width 194 relative to the shank diameter 206 may be selected such that when a threshold force is applied to the shank 202 in a direction aligned with the slot axis 192, the shank 202 will elastically deform (i.e., the resulting strain is below the yield strain of the material) the side walls 190 of the slot 128, thus permitting the shank 202 to escape from the second aperture 126 via the slot 128.

Because escapement of the shank 202 from the tether member 102 induces fully recoverable strain in the tether member 102, the shank 202 can be reengaged with the second aperture 126 with no loss in the threshold force required to induce another escapement. Furthermore, the threshold force may be selected such that it induces a corresponding restraining force on the physis 60 that is below the force that would induce growth from the physis 60 to "shut down." Alternatively, another embodiment (not shown) may have an escapement configuration that causes the slot side walls to permanently deform upon escapement of the coupling member from the tether member.

In addition to or in the alternative to interference between the shank 202 and the slot 128, the head 200 may interfere with passage of the head 200 through the slot 128. Specifically, the head 200 may have a head width 208, shown in FIG. 8A, at a portion of the head 200 that also passes through the slot 128, in addition to the shank 202. As more clearly shown in FIG. 7B, the slot 128 may have a shank-contacting portion 210 that will lie adjacent to the surface of the femur 58, and a head-contacting portion 212 further from the femur 58.

The shank-contacting portion 210 may provide interference with the shank 202 as described above. However, in some embodiments, given the polyaxially-adjustable adjustability of the orientation of the shank 202 relative to the tether member 102, interference between the shank 202 and the shank-contacting portion 210 may provide relatively unpredictable pullout force. Specifically, if the shank 202 is angularly displaced from perpendicularity with the tether member 102, the pullout force may be higher than if the shank 202 is perpendicular to the tether member 102.

Accordingly, it may be beneficial to have interference between the head 200 and the head-contacting portion 212. Thus, the head width 208 may be equal to or larger than the width of the head-contacting portion 212, at the depth at which the head 200 is to contact the head-contacting portion 212. FIG. 7A illustrates that the second aperture 126 may sweep across more than 180°. Thus, in order for the head 200 to escape the second aperture 126 and enter the slot 128, the head 200 may have to push hard enough on the adjoining shoulders 214 of the head-contacting portion 212 to push them apart, thereby increasing the width of the head-contacting portion 212 of the slot 128. The head 200 may then enter and pass through the slot 128, permitting the second end 112 to disengage from the corresponding one of the coupling members 104 as described above.

Figure 9:
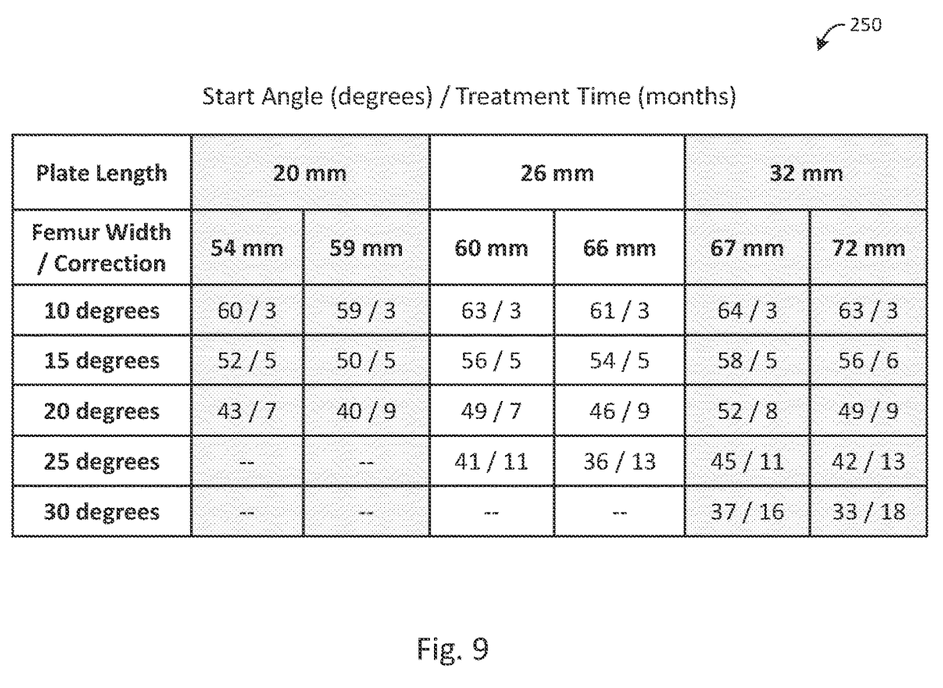
FIG. 9 is a table showing a relationship between correction angle, femur width, start angle, and treatment time for plate lengths of 20 mm, 26 mm and 32 mm, respectively.

FIG. 9 is a table 250 illustrating the start angle α (in degrees) and approximate treatment time (in months) that correspond to a rotational correction angle θ (in degrees), an average distal femur width (in mm) for a given length plate (in mm). The plate length provided in the table 250 is the distance 150 between a center of the first aperture 122 and a center of the second aperture 126, as shown in FIG. 5A.

All of the values in the table 250 are based on a constant end angle β of 70°. Using analytical geometry, similar tables can be developed for other values of end angle, start angle, treatment time, femur width, rotational correction angle and plate lengths as needed. For more severe deformities than provided in the table 250, multiple treatments may be applied to the same patient. For example, for a patient having 35° of rotational deformity and a 54 mm femur width, the surgeon can apply the tether member 102 at a start angle of 43° to achieve 20° of rotational correction in approximately 7 months. Then in a subsequent surgical procedure, the surgeon can remove and reapply the coupling members 104 and the tether member 102 (or a tether member 102 with a different size and/or contour) at a start angle of 52° to achieve another 15° of rotational correction in approximately 5 months. Thus, the patient undergoes a total of 35° of rotational correction in approximately 12 months.

The foregoing disclosure describes only selected embodiments encompassed within the scope of the disclosure. Those of skill in the art will recognize that the principles taught herein may be applied to generate many alternative concepts. For example, various clips, clasps, staples, plates, screws, and/or other fastening systems may be used to secure two sections of a bone together on either side of a growth plate. Such fastening systems may be made deliberately releasable, through detachable connections and/or breakable components, to effect release when the desired anteversion correction has been obtained.

Reference throughout this specification to "an embodiment" or "the embodiment" means that a particular feature, structure, or characteristic described in connection with that embodiment is included in at least one embodiment. Thus, the quoted phrases, or variations thereof, as recited throughout this specification are not necessarily all referring to the same embodiment.

Similarly, it should be appreciated that in the above description of embodiments, various features are sometimes grouped together in a single embodiment, figure, or description thereof for the purpose of streamlining the present disclosure. This method of disclosure, however, is not to be interpreted as reflecting an intention that any embodiment requires more features than those expressly recited in that embodiment. Rather, inventive aspects lie in a combination of fewer than all features of any single foregoing disclosed embodiment.

As used herein, the term "proximal" means a location at the end of a part that faces a user when the user is installing the part. The term "distal" means a location at the opposite end of the proximal end. For example, when a user installs a bone screw into a material with a driver, the end of the bone screw engaged with the driver is the proximal end, and the tip of the bone screw that first engages the material is the distal end. The term "cannulated" means having a central bore extending along a longitudinal axis of a part between a proximal end and a distal end of the part.

Recitation of the term "first" with respect to a feature or element does not necessarily imply the existence of a second or additional such feature or element. Elements recited in means-plus-function format are intended to be construed in accordance with 35 U.S.C. § 112(f). It will be apparent to those having skill in the art that changes may be made to the details of the above-described embodiments without departing from the underlying principles set forth herein.

The phrases "connected to," "coupled to" and "in communication with" refer to any form of interaction between two or more entities, including mechanical, electrical, magnetic, electromagnetic, fluid, and thermal interaction. Two components may be functionally coupled to each other even though they are not in direct contact with each other. The term "coupled" can include components that are coupled to each other via integral formation, as well as components that are removably and/or non-removably coupled with each other. The term "abutting" refers to items that may be in direct physical contact with each other, although the items may not necessarily be attached together. The phrase "fluid communication" refers to two or more features that are connected such that a fluid within one feature is able to pass into another feature. As defined herein the term "substantially" means within +/−20% of a target value, measurement, or desired characteristic.

While specific embodiments and applications of the present disclosure have been illustrated and described, it is to be understood that the scope of this disclosure is not limited to the precise configuration and components disclosed herein. Various modifications, changes, and variations which will be apparent to those skilled in the art may be made in the arrangement, operation, and details of the devices, systems, and methods disclosed herein.

What is claimed is:

1. A tether assembly configured to be attached to a bone comprising a growth plate that separates a first section of the bone from a second section of the bone, the tether assembly comprising:
    a first coupling member comprising:
        a first head; and
        a first shank comprising a first bone engagement feature configured to retain the first shank in the bone;
    a second coupling member comprising:
        a second head; and
        a second shank comprising a second bone engagement feature configured to retain the second shank in the bone; and
    a tether member comprising:
        a first end;
        a second end; and
        a central portion extending between the first end and the second end, wherein the central portion, together with the first end and the second end, defines a platelike shape;
    wherein:
        the first end comprises a closed outer wall that defines and fully bounds a first aperture;
        the second end comprises an open outer wall that defines and partially bounds a second aperture, the open outer wall defining a slot in communication with the second aperture;
        the first end is configured to be secured to the first section of the bone via the first coupling member inserted through the first aperture and anchored in the first section; and
        the second end is configured to be releasably secured to the second section of the bone via the second coupling member inserted through the second aperture and anchored in the second section such that the second end does not fully encircle the second shank and, in response to a threshold level of rotation of the first section of the bone relative to the second section of the bone, the second end is released from the second section of the bone.

2. The tether assembly of claim 1, wherein the second shank comprises a second shank width and the second head comprises a second head width, wherein the second shank width and/or the second head width is not smaller than a corresponding portion of the slot through which it must pass in order to exit the second aperture through the slot, such that the second coupling member is movable through the slot only in response to exertion of a threshold level of tension between the second coupling member and the second end, the threshold level of tension causing the corresponding portion of the slot to widen sufficiently to accommodate passage of the second shank and/or the second head therethrough.

3. The tether assembly of claim 2, wherein the corresponding portion of the slot is configured to deform elastically to permit passage of the second shank therethrough in response to exertion of the threshold level of tension.

4. The tether assembly of claim 1, wherein:
at least one of the first head and the second head comprises a first spherical surface; and
the corresponding one of the first aperture and the second aperture comprises a second spherical surface sized to receive the first spherical surface to provide adjustable positioning of the first head or the second head relative to the first aperture or the second aperture.

5. The tether assembly of claim 1, wherein the central portion comprises a contoured shape configured as a projection of an elongate area defined on a sagittal plane onto a medial epicondylar bone surface or a lateral epicondylar bone surface of a pediatric distal femur, the elongate area having a long axis and a short axis orthogonal to the long axis.

6. The tether assembly of claim 5, wherein:
the long axis as measured on the sagittal plane is positioned at an angle relative to a transverse plane; and
the angle is within the range of 30° to 60°.

7. The tether assembly of claim 1, wherein the slot is oriented nonperpendicular to a longitudinal length of the central portion.

8. The tether assembly of claim 7, wherein
the slot is oriented nonparallel to the longitudinal length.

9. A tether assembly configured to be attached to a bone comprising a growth plate that separates a first section of the bone from a second section of the bone, the tether assembly comprising:
a first coupling member comprising:
a first head; and
a first shank comprising a first bone engagement feature configured to retain the first shank in the bone;
a second coupling member comprising:
a second head; and
a second shank comprising a second bone engagement feature configured to retain the second shank in the bone; and
a tether member comprising:
a first end;
a second end; and
a central portion extending between the first end and the second end;
wherein:
the first end is configured to engage the first head to nonreleasably secure the first end to the first section of the bone; and
the second end is configured to engage the second head to releasably secure the second end to the second section of the bone such that the second end does not fully encircle the second shank and, in response to exertion of a threshold level of tension between the second coupling member and the second end, the second end is released from the second section of the bone.

10. The tether assembly of claim 9, wherein:
the first end comprises a fully-bounded first aperture; and
the second end comprises a partially-bounded second aperture that is accessible via a slot.

11. The tether assembly of claim 10, wherein the second shank comprises a second shank width that is not smaller than a slot width of the slot and is movable through the slot in response to exertion of the threshold level of tension, the threshold level of tension causing the corresponding portion of the slot to widen sufficiently to accommodate passage of the second shank and/or the second head therethrough.

12. The tether assembly of claim 11, wherein the slot is configured to deform elastically to permit passage of the second shank therethrough in response to exertion of the threshold level of tension.

13. The tether assembly of claim 10, wherein the slot is oriented nonperpendicular to a longitudinal length of the central portion.

14. The tether assembly of claim 9, wherein:
at least one of the first head and the second head comprises a first spherical surface; and
the corresponding one of the first end and the second end comprises a second spherical surface sized to receive the spherical surface to provide adjustable positioning of the first head or the second head relative to the first end or the second end.

15. The tether assembly of claim 9, wherein the central portion comprises a contoured shape configured as a projection of an elongate area defined on a sagittal plane onto a medial epicondylar bone surface or a lateral epicondylar bone surface of a pediatric distal femur, the elongate area having a long axis and a short axis orthogonal to the long axis.

16. A tether assembly configured to be attached to a bone comprising a growth plate that separates a first section of the bone from a second section of the bone, the tether assembly comprising:
a tether member comprising:
a first end;
a second end; and
a central portion extending between the first end and the second end, the central portion having a noncircular cross-sectional shape;
wherein:
the first end comprises a closed outer wall that defines and fully bounds a first aperture;
the second end comprises an open outer wall that defines and partially bounds a second aperture, the open outer wall defining a slot, narrower than the second aperture, in communication with the second aperture;
the first end is configured to be secured to the first section of the bone via a first coupling member inserted through the first aperture and anchored in the first section; and the second end is configured to be secured to the second section of the bone via a second coupling member inserted through the second aperture and anchored in the second section.

17. The tether assembly of claim 16, further comprising:
the first coupling member comprising:
a first head; and
a first shank comprising a first bone engagement feature configured to retain the first shank in the bone; and
the second coupling member comprising:
a second head; and
a second shank comprising a second bone engagement feature configured to retain the second shank in the bone;
wherein:
the second shank comprises a second shank width and the second head comprises a second head width, wherein the second shank width and/or the second head width is not smaller than a corresponding portion of the slot through which it must pass in order to exit the second aperture through the slot, such that the second coupling member is movable through the slot only in response to exertion of a threshold level of tension between the second coupling member and the second end; and
the corresponding portion of the slot is configured to deform elastically to permit passage of the second shank therethrough in response to exertion of the threshold level of tension.

18. The tether assembly of claim 16, wherein:
the central portion comprises a contoured shape created by projecting an elongate area configured to be defined on a sagittal plane onto a medial epicondylar bone surface or a lateral epicondylar bone surface of a pediatric distal femur, the elongate area having a long axis and a short axis orthogonal to the long axis;
the long axis as measured on the sagittal plane is positioned at an angle relative to a transverse plane; and
the angle is within the range of 30° to 60°.

19. The tether assembly of claim 16, wherein:
the slot is oriented nonperpendicular to a longitudinal length of the central portion;
the slot is oriented at an angle relative to the longitudinal length; and
the angle is within the range of 0° to 80°.

20. A tether assembly configured to be attached to a bone comprising a growth plate that separates a first section of the bone from a second section of the bone, the tether assembly comprising:
a tether member comprising:
a first end;
a second end; and
a central portion extending between the first end and the second end, wherein the central portion, together with the first end and the second end, defines a platelike shape;

wherein:
the first end comprises a closed outer wall that defines and fully bounds a first aperture;
the second end comprises an open outer wall that defines and partially bounds a second aperture, the open outer wall defining a slot in communication with the second aperture;
the first end is configured to be secured to the first section of the bone via a first coupling member inserted through the first aperture and anchored in the first section;
the second end is configured to be secured to the second section of the bone via a second coupling member inserted through the second aperture and anchored in the second section; and
the slot is oriented nonparallel and nonperpendicular to a longitudinal length of the central portion.

21. The tether assembly of claim 20, further comprising:
the first coupling member comprising:
a first head; and
a first shank comprising a first bone engagement feature configured to retain the first shank in the bone; and
the second coupling member comprising:
a second head; and
a second shank comprising a second bone engagement feature configured to retain the second shank in the bone.

22. The tether assembly of claim 21, wherein the second shank comprises a second shank width and the second head comprises a second head width, wherein the second shank width and/or the second head width is not smaller than a corresponding portion of the slot through which it must pass in order to exit the second aperture through the slot, such that the second coupling member is movable through the slot only in response to exertion of a threshold level of tension between the second coupling member and the second end, the threshold level of tension causing the corresponding portion of the slot to widen sufficiently to accommodate passage of the second shank and/or the second head therethrough.

23. The tether assembly of claim 22, wherein the corresponding portion of the slot is configured to deform elastically to permit passage of the second shank therethrough in response to exertion of the threshold level of tension.

24. The tether assembly of claim 21, wherein:
at least one of the first head and the second head comprises a first spherical surface; and
the corresponding one of the first aperture and the second aperture comprises a second spherical surface sized to receive the first spherical surface to provide adjustable positioning of the first head or the second head relative to the first aperture or the second aperture.

\* \* \* \* \*